United States Patent [19]

Lu et al.

[11] Patent Number: 4,636,517

[45] Date of Patent: Jan. 13, 1987

[54] 3-TOLYLTHIO-4-AMINO-4,5-DIHYDRO ISOXAZOLE AS ANTHELMINTIC

[75] Inventors: Jing-Jong Lu; Herbert L. Wehrmeister, both of Terre Haute, Ind.

[73] Assignee: International Minerals & Chemical Corp., Terre Haute, Ind.

[21] Appl. No.: 788,934

[22] Filed: Oct. 18, 1985

[51] Int. Cl.$^4$ ................... A61K 31/42; C07D 261/04
[52] U.S. Cl. ............................. 514/380; 548/244
[58] Field of Search ............... 548/244; 514/380

[56] References Cited

U.S. PATENT DOCUMENTS

| | | | |
|---|---|---|---|
| 3,629,474 | 12/1971 | Ghosh et al. | 514/376 |
| 3,687,968 | 8/1972 | Iwai et al. | 548/243 |
| 3,879,532 | 4/1975 | Hass et al. | 514/378 |
| 3,879,533 | 4/1975 | Carr et al. | 514/378 |
| 4,010,176 | 3/1977 | Kulsa et al. | 548/248 |
| 4,062,861 | 12/1977 | Yukinaga et al. | 548/246 |
| 4,137,321 | 1/1979 | Leeming et al. | 514/368 |
| 4,275,214 | 6/1981 | Kelly et al. | 548/243 |
| 4,322,429 | 3/1982 | Burow | 514/378 |
| 4,336,264 | 6/1982 | Wickiser | 514/378 |
| 4,593,024 | 6/1986 | Lu et al. | 514/234 |

FOREIGN PATENT DOCUMENTS 259933 2/1968 Austria.
2068418 8/1971 France.

*Primary Examiner*—Donald G. Daus
*Assistant Examiner*—Barbara Cassatt
*Attorney, Agent, or Firm*—Wendell R. Guffey; Thomas L. Farguer

[57] ABSTRACT

A novel tolylthioisoxazole compound is disclosed having activity against the pinworms *S. obvelata* and *A. tetraptera*. A process for making these compounds and a method of administering it to infested animals is also disclosed.

7 Claims, No Drawings

3-TOLYLTHIO-4-AMINO-4,5-DIHYDRO ISOXAZOLE AS ANTHELMINTIC

BACKGROUND OF THE INVENTION

Parasitic worms afflict mammals and fowl and thus pose an economic problem in the raising of cattle, swine, poultry and fur-bearing mammals. A significant number of compounds containing an amidine structural feature have shown significant anthelmintic activity, e.g., levamisole, albendazole, thiabendazole, morantel and bunamidine. However, a compounds that is active against one type of worm is not necessarily active against other types. Likewise, toxicity often varies from one host animal to the next. Therefore, there is a need for new agents with activities against a broad spectrum of endoparasitic worms and with low toxicity toward the host.

Numerous isoxazoles, isoxazolines and isoxazolidines have been isolated from natural sources or synthesized, and individual compounds or closely-related groups of compounds have been reported to be active as herbicides, or anti-protozoan drugs, or hypoglycemic agents, or anti-inflammatory agents or anti-pyretic agents. It is obvious that having activity against one particular pest or biological dysfunction does not mean a compound will also be active against parasitic worms. In addition, the activity of a compound even against a single pest is almost impossible to predict from its structure. For example, two structurally similar compounds can have dramatically different anthelmintic activities, one being very effective and the other totally ineffective.

SUMMARY OF THE INVENTION

It is an object of the invention to provide a new compound having anthelmintic activity.

It is an additional object of the present invention to provide a new compound having activity with low toxicity against gastrointestinal nematode infestations and cestode infestations in animals.

It is a further object of the invention to provide a process for synthesizing the new compound.

It is another object of this invention to provide a method of treating mammals or fowl which are infested with parasitic worms or treating mammals or fowl to prevent infestation by parasitic worms.

In accordance with this invention there is provided an anthelmintic compound of the formula:

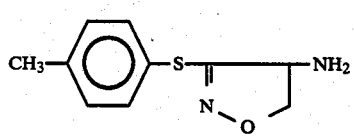

In other embodiments of this invention there are provided a method of making the claimed compound, as well as a method of feeding animals with the claimed compound.

When used at an effective dosage, the compound of the present invention causes little or no toxicity to the host animals. This provides an obvious benefit in the husbandry of these animals.

DETAILED DESCRIPTION OF THE INVENTION

It has been found that tolylthioisoxazoline of the formula

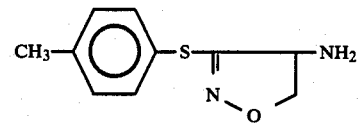

has good activity in controlling infestations by the pinworms *S. obvelata* and *A. tetraptera* in infested animals without harm to the host animal, at an effective dosage.

The compound of this invention can be prepared from D-cycloserine by first protecting the active amino group by reacting D-cycloserine with a phthaloyl-containing compound to form a phthalamide with the 4-amino group of D-cycloserine. One appropriate means is the use of N-carboethoxyphthalimide as the phthaloyl-containing compounds as reported by Nefkens (Nature, 185, 309, 1960). This reaction can be carried out in the presence of sodium carbonate in aqueous solution at room temperature. Alternative methods of protecting the active amino group include using O-methoxy-carbonylbenzoyl chloride as the phthaloyl-containing compounds instead of N-carboethoxyphthalimide, as described by Hoogwater (Racueil de Travaux Chimiques de Pays-Bas, 92, 819-825, 1973), and via silylation followed by reaction with phthaloylchloride, as described by Kume (Tetrahedron Letters, 23, 4365 1982).

After the amino group has been protected, the ring system can be modified by reaction with a phosphorous chloride. For example, the corresponding imidoyl chloride, 3-chloro-4-phthalimido-4,5-dihydroisoxazole, can be formed by reaction with phosphorous oxychloride, as described in J. Amer. Chem. Soc. 103, 942 (1981). Alternative methods of forming the imidoyl chloride include reaction with phosphorous pentachloride in refluxing nitromethane. This however is a harsher method and tends to result in a lower yield of desired product and the formation of the undesired by-product 3-(3-keto-4-phthalimidoisoxazoline-2-yl)-4-phthalimido-isoxazoline.

The imidoyl chloride, 3-chloro-4-phthalimido-4,5-dihydroisoxazole, is a useful intermediate which can be used to make the compounds of this invention.

To form the compound of the present invention, the imidoyl chloride is reacted with thiocresol. The reaction may be carried out in any suitable solvent system and proceeds even at room temperature. For example, the imidoyl chloride may be dissolved in ethanol and the thiocresol dissolved in triethylamine. After mixing together, the reaction is permitted to proceed to room temperature for about four hours. Thus the chlorine atom is replaced by nucleophilic substitution with a tolylthio group.

Thereafter the phthalimide protecting group is displaced by reaction with hydrazines, such as methylhydrazine, but other agents known in the art can be used as well. This reaction is carried out in a suitable solvent, such as tetrahydrofuran and methanol, at room temperature for about two hours.

To recover the reaction product, a salt can be formed with any pharmaceutically appropriate acid; for example, the oxalate salt can be readily prepared by reaction of the free amine compounds with oxalic acid. Formation of the salt stabilizes the compounds at room temperature. The salt can be further purified by recrystallization from an appropriate solvent such as isopropyl alcohol. If the compound is to be used as the free amine compound, it normally must be refrigerated to insure stability.

Parasitic worms afflict both mammals and birds, therefore the present invention is useful in the raising and husbandry of livestock such as cattle, swine, sheep and goats, domestic pets such as dogs and cats, rabbits, poultry such as turkeys, chickens, geese and ducks, and fur-bearing aminals such as foxes, mink and chinchilla. The compound of the present invention can be administered orally by conventional means and techniques known in the art. It can be used prophylactically to protect animals or therapeutically after the animals have been infested.

In general, prophylactic dosages will be lower than those for pre-existing infestations. For example, dosages as low as 1 mg/kg of body weight may be sufficient to protect an animal from infestation by parasitic worms. Therapeutic dosages will often be from 10 to 100 times greater than prophylactic dosages.

The dosage used will depend on: (1) the animal to be treated; (2) the timing of administration; and (3) the method of administration. Determination of the proper dosage in light of these variables is within the control and competence of one skilled in the art.

The chemotherapeutic agent of this invention can be administered in any of a variety of forms, alone or in combination, with other pharmaceuticals. It can be administered in a solid form or in liquid form in a suitable solvent. For example, it may be administered orally in admixture with an animal feed or fed separately as a supplement. Appropriate amounts of anthelmintic compounds for therapeutic treatment of pre-existing infestations are often from about 300 ppm to about 2000 ppm of animal feed.

Suitable dosages are often from about 0.5 to about 200 mg of active ingredient per kg of body weight of the host animal, depending on the infesting pest, the degree of infestation, and the program of administration.

EXAMPLE 1

Phthaloylation of D-cycloserine with N-carboethoxyphthalimide

D-cycloserine (15.3 g, 0.15 mol) and sodium carbonate (15.9 g, 0.15 mol) were dissolved in 200 ml of water. N-Carboethoxyphthalimide (36.0 g, 0.164 mol) was added to the solution and the mixture was stirred at room temperature for 25 minutes and filtered to remove unreacted N-carboethoxyphthalimide (12.1 g). The filtrate was chilled on ice bath and acidified with 4N HCl. Phthaloyl-D-cycloserine (18.5 g) precipitated out of solution and was collected by filtration, air dried, and recrystallized from ethyl acetate.

EXAMPLE 2

The synthesis of 3-chloro-4-phthalimido-4,5-dihydroisoxazole

The compounds prepared in Example 1, phthaloyl-D-cycloserine (9.28 g, 40 mmol), was dissolved in 100 ml of nitromethane. Phosphorous oxychloride (4 ml, 43 mmol) was added to the solution, which was then heated to 100° C. in a two-hour period and kept at that temperature for an additional hour. The mixture was cooled to room temperature, and the solids were filtered off. The filtrate was concentrated, and the residue was extracted with ethyl acetate. The solvent was removed and the product was purified by flash chromatography and eluted with 3:1 petroleum ether/ethyl acetate to yield 3-chloro-4-phthalimido-4,5-dihydroisoxazole (5.49 g).

EXAMPLE 3

The preparation of 3-(p-tolylthio)-4-phthalimido-4,5-dihydroisoxazole

3-Chloro-4-phthalimido-4,5-dihydroisoxazole (2.0 g, 8 mmol) was dissolved in 50 ml of ethanol (3A grade) and cooled to 0°–5° C. on ice bath. A solution of thiocresol (1.0 g, 8 mmol) in 30 ml of triethylamine was added to the first solution. The reaction mixture was stirred at room temperature for 4 hours. The reaction product was purified by flash chromatography on silica gel (230–400 mesh), eluted with 2:1 petroleum ether/ethyl acetate and collected in 20 ml fractions. Unreacted thiocresol eluted in fractions 2–6, and the reaction product 3-(p-tolylthio)-4-phthalimido-4,5-dihydroisoxazole (1.65 g, 60.95%) was eluted in fractions 8–32.

EXAMPLE 4

Removal of the phthaloyl protecting group 3-(p-Tolylthio)-4-phthalimido-4,5-dihydroisoxazole (0.338 g, 1 mmol) was dissolved in 20 ml of tetrahydrofuran and 20 ml of methanol. Methylhydrazine (0.46 g, 10 mmol) was added to the solution dropwise. The reaction was stirred at room temperature for 2 hours. The solvents and unreacted methylhydrazine were removed by evaporation. The residue, containing 3-p-tolylthio-4-amino-4,5-dihydroisoxazole, was dissolved in 30 mls of isopropyl alcohol.

EXAMPLE 5

Preparation of oxalate salt of 3-p-tolylthio-4-amino-4,5-dihydroisoxazole

The dissolved residue, produced in Example 4 was added to oxalic acid (0.09 g, 1 mmol) in 30 ml of isopropyl alcohol. The solution was kept at 4° C. overnight. The oxalate salt of 3-p-tolylthio-4-amino-4,5-dihydroisoxazole was filtered off and recrystallized from isopropyl alcohol.

EXAMPLE 6

The product described in Example 4 has been given to worm-infested mice in the diet, and the reduction in worm number has been recorded. At dosage levels of 1000 ppm of feed, 3-p-tolylmercepto-4-phthalimido-4,5-dihydroisoxazole caused a 75% reduction in burden of *S. obvelata*, and a 37% reduction in burden of *A. tetraptera*. The feed was given daily. No toxicity was observed when this compound was injected into mice intraperitoneally at a dosage level of 100 mg/kg of body weight.

What is claimed is:

1. An anthelmintic compound of the formula:

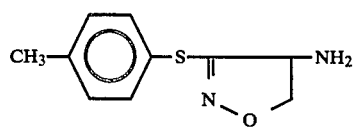

2. The oxalate salt of the compound of claim 1.

3. A method of treating mammals and fowl which are infested with parasitic worms which comprises administering orally the anthelmintic compound 3-tolylthio-4-amino-4-5-dihydroisoxazole to said infested animals.

4. The method of claim 3 wherein said compound is administered in admixture with feed in an amount of from about 300 to about 2,000 ppm.

5. The method of claim 3 wherein said compound is administered in a dosage of from about 0.5 to about 200 mg of active ingredient per kg of animal body weight.

6. A method of treating mammals and fowl to prevent infestation by parasitic worms which comprises administering orally the anthelmintic compound, 3-tolylthio-4-amino-4-5-dihydroisoxazole to said animals.

7. The method of claim 6 wherein said compound is administered in admixture with feed in an amount of from about 300 to about 2,000 ppm.

* * * * *